(12) United States Patent
Solar et al.

(10) Patent No.: US 8,109,897 B2
(45) Date of Patent: Feb. 7, 2012

(54) METHOD FOR SELECTIVE THERMAL TREATMENT

(75) Inventors: Ronald J. Solar, San Diego, CA (US); Glen Lieber, Poway, CA (US)

(73) Assignee: ThermopeutiX, Inc., San Diego, CA (US)

( * ) Notice: Subject to any disclaimer, the term of this patent is extended or adjusted under 35 U.S.C. 154(b) by 0 days.

(21) Appl. No.: 12/731,222

(22) Filed: Mar. 25, 2010

(65) Prior Publication Data

US 2010/0179466 A1    Jul. 15, 2010

Related U.S. Application Data

(60) Division of application No. 11/338,892, filed on Jan. 25, 2006, now Pat. No. 7,704,220, which is a continuation-in-part of application No. 11/041,701, filed on Jan. 25, 2005, now Pat. No. 7,789,846.

(51) Int. Cl.
*A61M 1/00* (2006.01)
(52) U.S. Cl. ....... 604/28; 604/4.01; 604/6.13; 604/6.16; 604/96.01; 604/113; 604/506
(58) Field of Classification Search ................ 604/4.01, 604/6.13, 6.16, 7, 8, 27, 506, 507, 508, 509, 604/96.01, 102.01, 102.03, 113, 114
See application file for complete search history.

(56) References Cited

U.S. PATENT DOCUMENTS

| | | | |
|---|---|---|---|
| 6,435,189 B1 * | 8/2002 | Lewis et al. | 128/898 |
| 6,508,777 B1 * | 1/2003 | Macoviak et al. | 604/4.01 |
| 2003/0009146 A1 * | 1/2003 | Muni et al. | 604/500 |
| 2004/0236350 A1 | 11/2004 | Lewis et al. | |
| 2005/0004503 A1 | 1/2005 | Samson et al. | |

FOREIGN PATENT DOCUMENTS

| | | |
|---|---|---|
| JP | B 0002683750 | 1/1990 |
| JP | A 1993220215 | 8/1993 |
| JP | A 1997511155 | 11/1997 |
| JP | A 2002501792 | 1/2002 |
| JP | A 2004305251 | 11/2004 |
| WO | WO 00/74749 | 12/2000 |
| WO | WO 2004/075928 | 9/2004 |

\* cited by examiner

*Primary Examiner* — Bhisma Mehta
(74) *Attorney, Agent, or Firm* — Daniel J. Swirsky; AlphaPatent Associates Ltd.

(57) ABSTRACT

Methods for selective cooling or heating of a target site in the human body include a catheter having a supply elongated element and a delivery elongated element, with inlet and exit ports. Blood is withdrawn from the supply elongated element and cooled or heated in a control unit. The treated blood is sent to the targeted area via delivery elongated element. The supply elongated element can act as an insulator for the treated blood in the delivery elongated element.

22 Claims, 18 Drawing Sheets

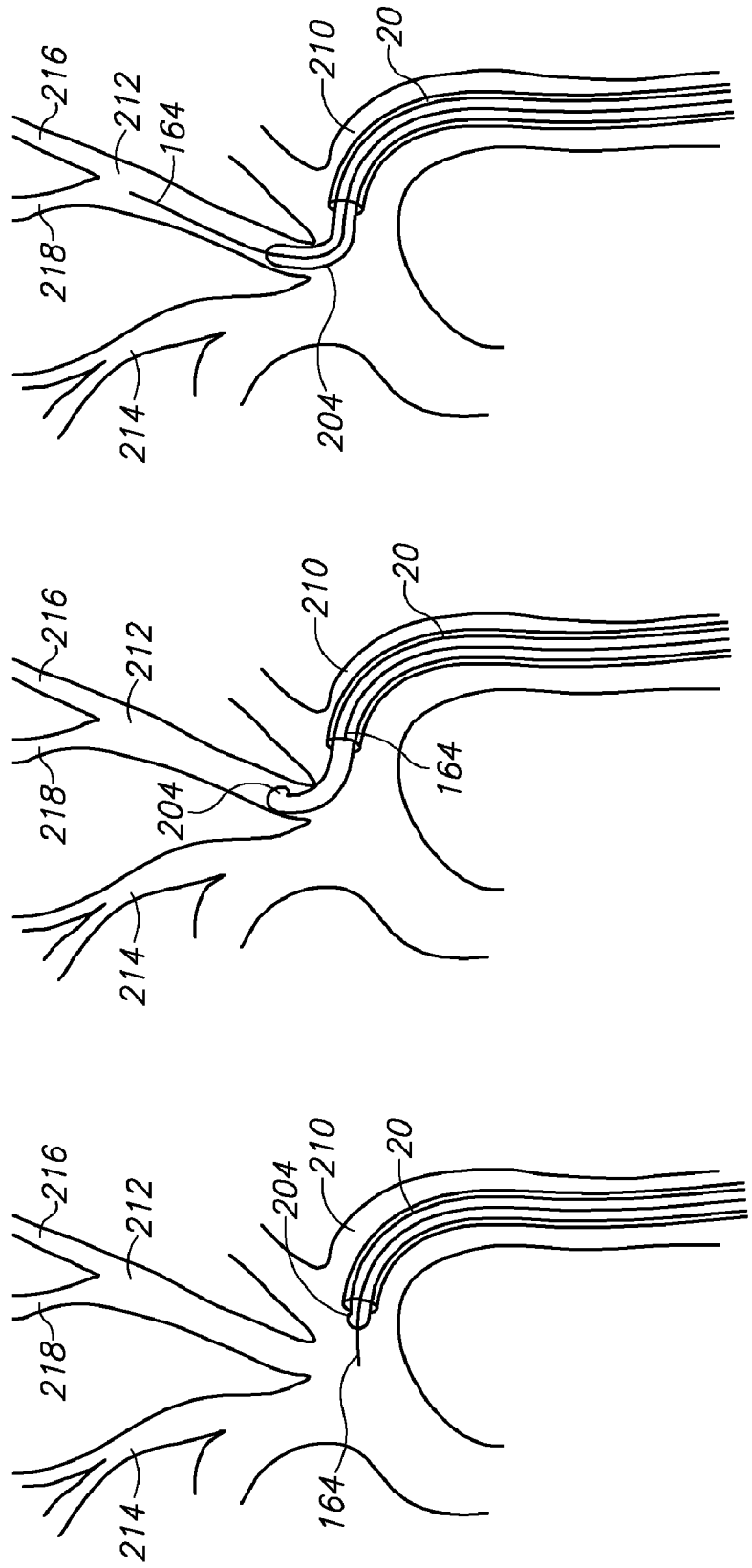

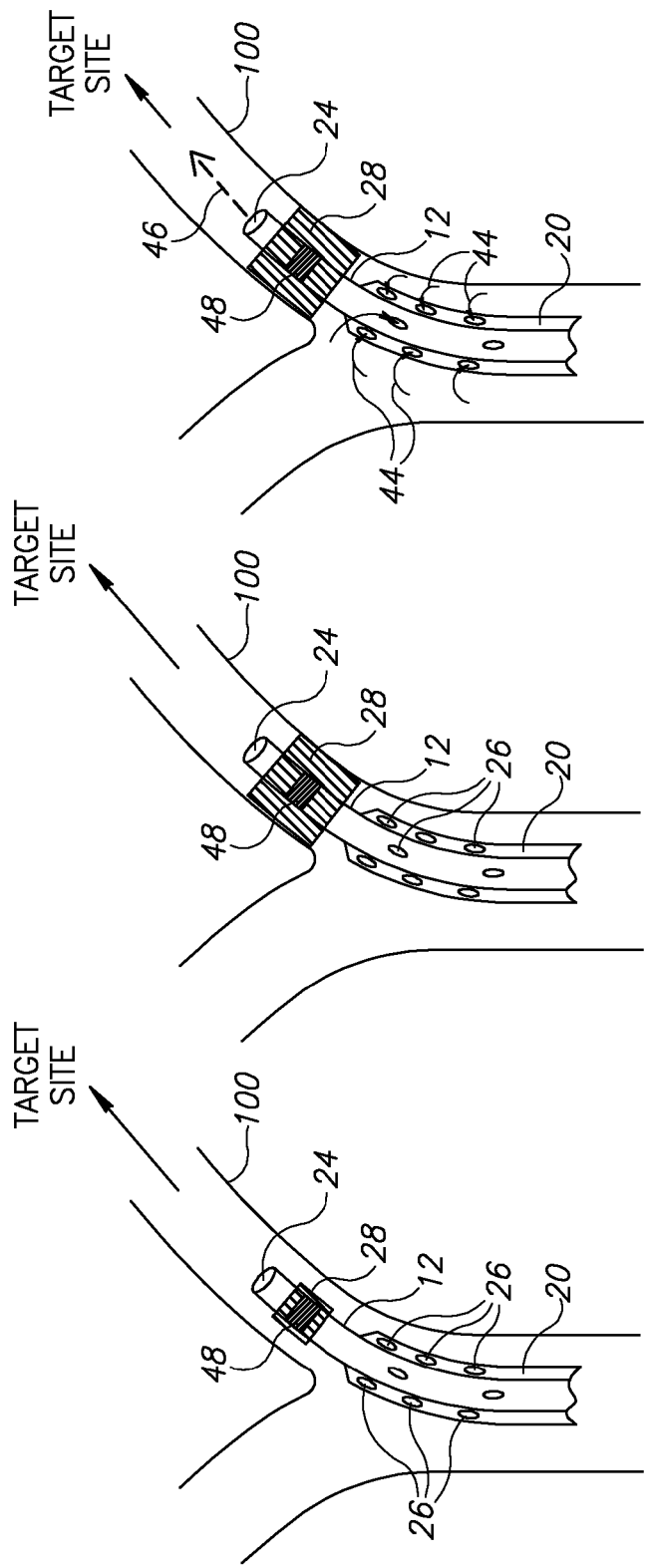

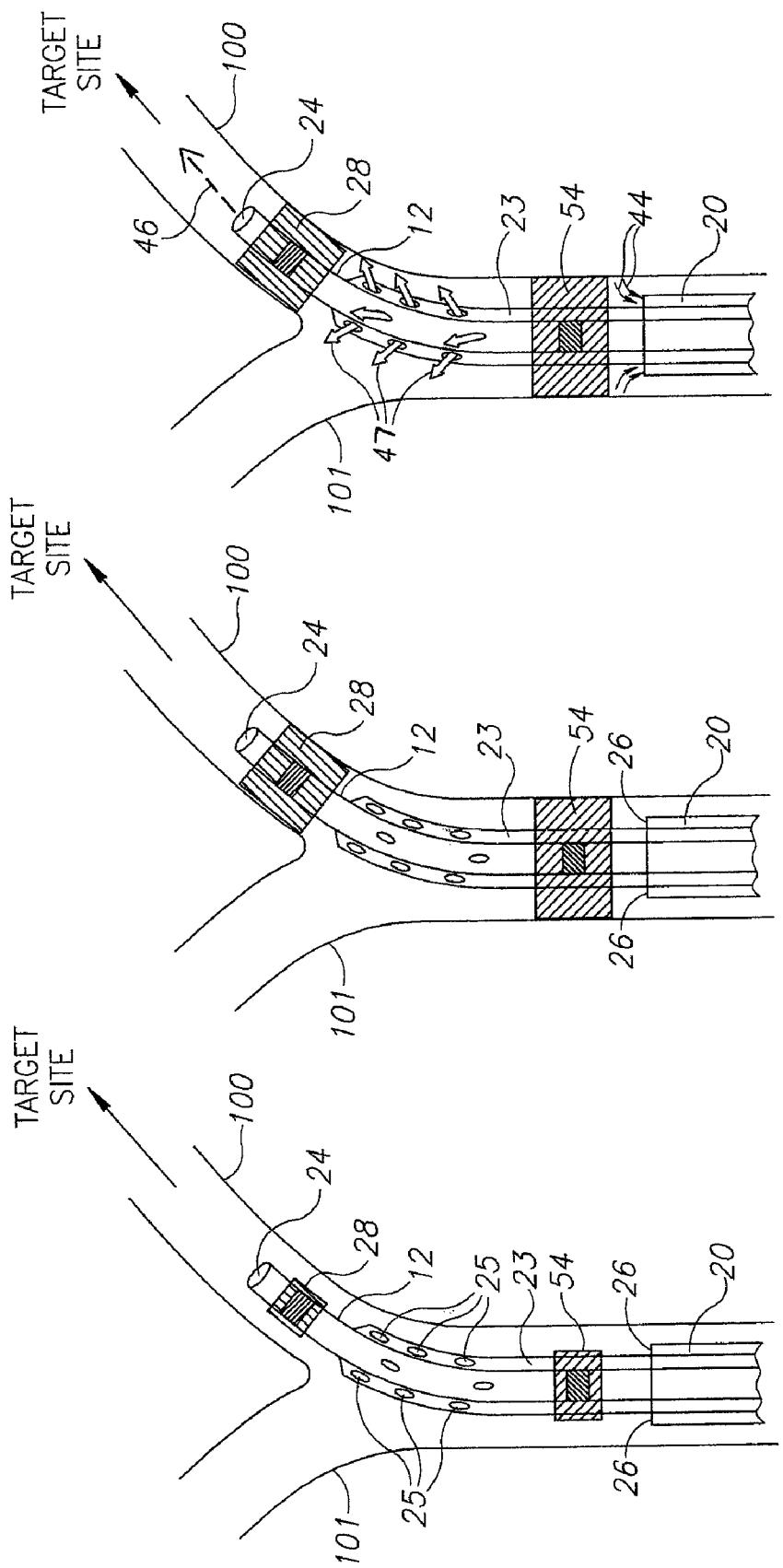

METHOD FOR SELECTIVE THERMAL TREATMENT

CROSS-REFERENCES TO RELATED APPLICATIONS

The present application is a divisional of U.S. patent application Ser. No. 11/338,892, filed on Jan. 25, 2006, now U.S. Pat. No. 7,704,220, which is a continuation-in-part of U.S. patent application Ser. No. 11/041,701, filed on Jan. 25, 2005, now U.S. Pat. No. 7,789,846, both of which applications are incorporated by reference herein in their entirety.

FIELD AND BACKGROUND OF THE INVENTION

The present invention relates to methods for selectively treating a target site in the body, specifically by changing a temperature thereof, and without significantly affecting other parts of the body.

It is generally known that many disease states and injuries respond favorably to the application of heat and/or cold. For example, hypothermia, i.e. cooling, can reduce blood flow, inflammation and edema, and may alter a variety of effects of ischemia. On the cellular level, hypothermia and hyperthermia (heating) have the ability to effect metabolic and enzymatic activity, reactive oxidant production and gene expression. A number of experimental studies of ischemic stroke have shown that hypothermia reduces the extent of neurologic damage and improves neurologic function.

Prior art methods to effect hypothermia or hyperthermia have a number of disadvantages. Most of these methods primarily involve the entire body by employing surface techniques or systemic intravascular perfusion. U.S. Pat. No. 5,624,392 to Saab and U.S. Pat. No. 6,033,383 to Ginsburg teach the use of heat transfer catheters that are placed into the venous side of the vascular system. These devices cool or heat venous blood passing over them, and the heated or cooled blood is distributed throughout the entire body. Such methods have serious limitations. For example, systemic hypothermia causes shivering, which increases the metabolic rate and may cause serious disturbances of the cardiovascular system. Surface techniques are slow, have limited heating/cooling capability, and require apparatus that can interfere with the ability to perform a medical procedure. In addition, none of these prior art techniques have the ability to control changes in blood flow and pressure that can result from the application of hypothermia or hyperthermia, nor do they have means to administer pharmacologic agents selectively to the target area.

Other prior art methods designed to selectively treat an area without adversely affecting the rest of the body have been disclosed. For example, U.S. Pat. Nos. 6,436,071 and 6,605, 106 to Schwartz teach a catheter for intravascular corporeal cooling, designed to eliminate problems that develop due to complications from high pressure within a delivery catheter. This disclosure teaches the use of a pressure relief valve, which has the disadvantage of a likelihood of total body cooling upon activation of the valve. Additionally, long-term effects of the disclosed system can include potential local vascular damage, and additional total body cooling, since arterial blood passing over the cooling catheter would itself be cooled. U.S. Pat. No. 6,042,559 to Dobak teaches a method and apparatus for performing hypothermia without significant effect on surrounding organs or other tissues. The disclosed apparatus includes a flexible supply catheter, and a separate flexible delivery catheter—one used for removing the blood and one used for delivering cooled blood into an artery feeding the selected organ. The delivery catheter has a layer of insulation. However, the use of two catheters increases the risk of vascular complications, the complexity of the procedure, and the time to effect cooling of the target organ.

There is thus a widely recognized need for, and it would be highly advantageous to have, a method for selective thermal treatment which is devoid of the above limitations.

SUMMARY OF THE INVENTION

According to one aspect of the invention there is provided a method for selectively cooling or heating a part of a body. The method includes providing a device for insertion into a vessel, the device having a first lumen and an exit port, a second lumen and a second port, wherein the second lumen is positioned coaxial to the first lumen, and an occlusion element positioned between the exit port and the second port, inserting the device into a vessel, expanding the occlusion element so as to separate between a first area in fluid communication with the exit port and a second area in fluid communication with the second port, withdrawing normothermic blood from the second area via the second port and through the second lumen, delivering the normothermic blood to a control unit, thermally treating the normothermic blood in the control unit to obtain thermally treated blood, and delivering the thermally treated blood to the first area via the first lumen and the exit port.

According to yet another aspect of the invention there is provided a method for insulating thermally treated blood for delivery to a location in the body. The method includes providing a delivery catheter having a delivery lumen and a supply lumen which is coaxial to the delivery lumen, inserting the delivery catheter into the arterial system, withdrawing normothermic blood from the arterial system via the supply lumen, simultaneously providing thermally treated blood via the delivery lumen to the arterial system, the simultaneous providing being in a location which is distal to a location of the withdrawing, wherein the withdrawing is done coaxial to the simultaneous providing thermally treated blood, thus providing a layer of insulation to the thermally treated blood.

According to yet another aspect of the invention there is provided a method for positioning of a thermal treatment catheter in a target artery. The method includes positioning a guidewire in a proximal artery which is proximal to the target artery, introducing a search catheter over the guidewire, partially withdrawing the guidewire, locating the target artery with the search catheter, advancing the guidewire through the search catheter and into the target artery, removing the search catheter, and advancing a distal end of the thermal treatment catheter over the guidewire into the target artery.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 9A-9H are illustrations of the steps of a method of positioning a catheter in a vessel in accordance with additional embodiments of the present invention;

FIGS. 11A-11C are illustrations of the steps of a method for treating a specific target site in accordance with one embodiment of the present invention;

FIGS. 12A-12C are illustrations of a method for treating a specific target site in accordance with another embodiment of the present invention.

DETAILED DESCRIPTION OF THE INVENTION

Figure 1A:
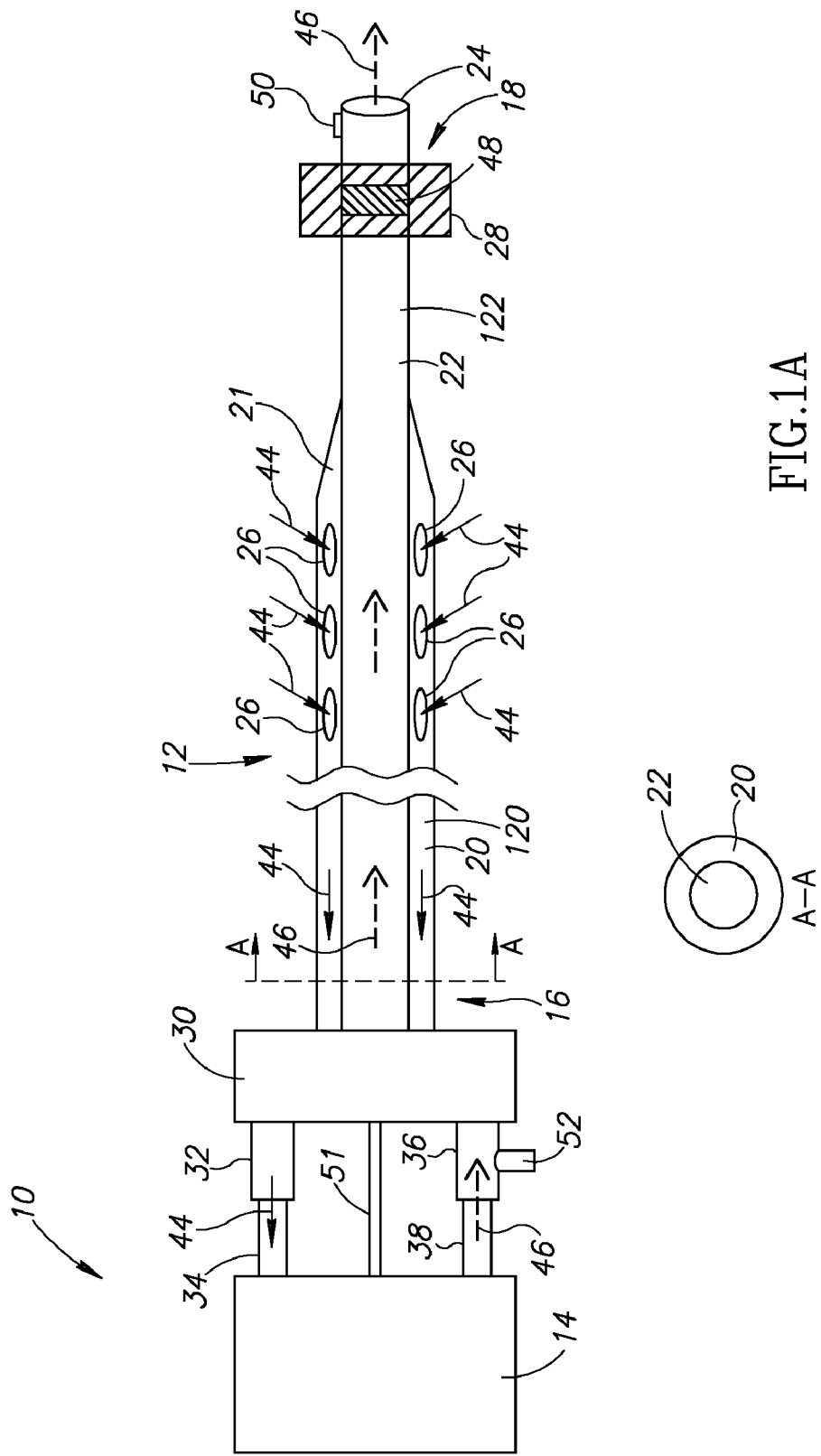
FIG. 1A is an illustration of a system including a catheter and a control unit, in accordance with one embodiment of the present invention.

The present invention is of systems and methods which can be used for selective thermal therapy. Specifically, the present invention can be used to selectively cool or heat a specific organ in the body, using a single catheter for collection and delivery of normothermic and thermally altered blood.

The principles and operation of systems and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
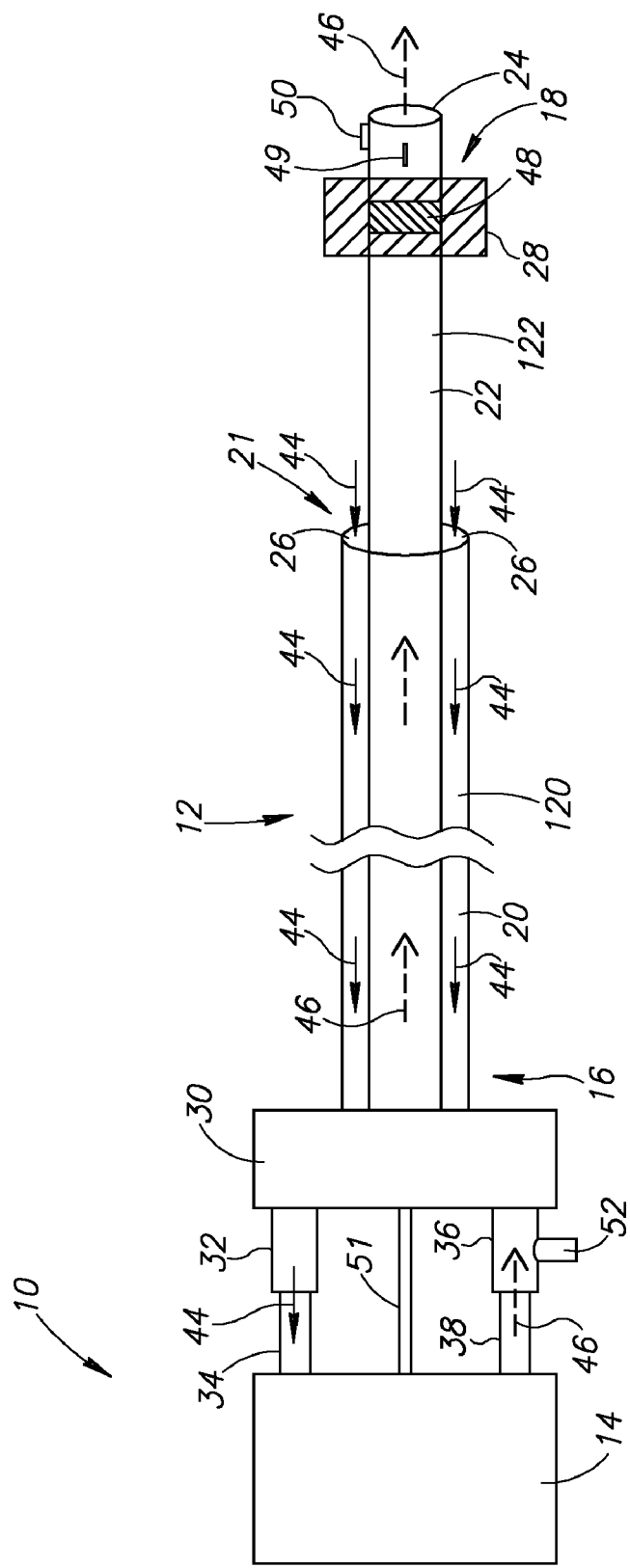
FIG. 1B is an illustration of a system including a catheter and a control unit, in accordance with another embodiment of the present invention.

Referring now to the drawings, FIGS. 1A and 1B illustrate a system 10 for selective cooling or heating of an organ, in accordance with preferred embodiments of the present invention. System 10 includes a catheter 12 and a control unit 14. Catheter 12 has a proximal end 16 and a distal end 18, and includes a supply elongated element 20 having a supply lumen 120 therethrough and a delivery elongated element 22 having a delivery lumen 122 therethrough. Delivery elongated element 22 is preferably an elongated tubular member, extending through an entire length of catheter 12, from proximal end 16 to distal end 18, and has an exit port 24 at or near distal end 18 for delivery of blood to a target site. Supply elongated element 20 is preferably an elongated tubular member which is positioned coaxially with respect to delivery elongated element 22, as shown in cross-section A-A, and extends from proximal end 16 of catheter 12 to an area proximal to distal end 18, wherein supply elongated lumen 20 extends along a majority of a length of delivery elongated lumen 22. In an alternative embodiment, supply elongated element 20 runs alongside delivery elongated element 22. In one embodiment, as shown in FIG. 1A, supply elongated element 20 has inlet ports 26 at one or more locations along its length, for receiving normothermic blood from the blood vessel. In a preferred embodiment, as shown in FIG. 1B, supply elongated element 20 has an inlet port 26 located at a distal end 21 thereof. In this embodiment, inlet port 26 is created by the coaxial arrangement of supply elongated element 20 and delivery elongated element 22, wherein an inner diameter of supply elongated element 20 is sized at least 0.1 mm greater than an outer diameter of delivery elongated element 22. The space created by this difference in diameter creates a port which is sufficiently sized for receiving supply blood from the vessel, as will be described in greater detail hereinbelow. In a preferred embodiment, an outer diameter of delivery elongated element 22 is in a range of 0.081 inches to 0.128 inches and an inner diameter of supply elongated element 20 is in a range of 0.100 inches to 0.162 inches.

As shown in FIGS. 1A and 1B, at least one occlusion element 28 is positioned at or near distal end 18 of catheter 12, proximal to exit port 24 and distal to a distal end 21 of supply elongated element 20. A hub 30 for connecting supply elongated element 20 and delivery elongated element 22 to control unit 14 is located at proximal end 16 of catheter 12. Hub 30 includes an inlet connector 32 for providing supply blood to a supply blood inlet 34 in control unit 14, and an outlet connector 36 for receiving delivery blood from a delivery blood outlet 38 in control unit 14. Control unit 14 thermally alters (i.e. heats or cools) normothermic blood received from supply blood inlet 34, and sends the thermally altered blood out through delivery blood outlet 38. Catheter 12 can be introduced over a guidewire, either as an over-the-wire system or as a rapid exchange system, or may include a fixed wire at its distal tip. In a preferred embodiment, delivery elongated element 22 acts as a guidewire lumen as well. In alternative embodiments, a separate guidewire lumen is positioned alongside or coaxial with delivery elongated element 22. In the fixed-wire configuration, catheter 12 could further include a torqueable catheter shaft. In one embodiment, such as the one depicted in FIG. 1B, delivery elongated element 22 and supply elongated element 20 are detachable from and/or movable with respect to one another.

The general cycle of blood flow is as follows. Normothermic blood, depicted by unbroken arrows 44, flows from a blood vessel, through at least one inlet port 26, and into supply elongated element 20. Supply elongated element 20 delivers the normothermic blood to control unit 14 via inlet connector 32. Blood is then thermally altered in control unit 14. Delivery elongated element 22 receives thermally altered blood, depicted by broken arrows 46, from delivery blood outlet 38 in control unit 14 via outlet connector 36, and delivers the thermally altered blood to the target site in the body. In order to ensure that heating or cooling of the target site is accomplished without causing heating or cooling of other parts of the body, it is necessary to physically separate the collection of normothermic blood from the delivery of thermally altered blood. In order to accomplish this separation using a single device, catheter 12 is designed with both a supply elongated element and a delivery elongated element having an occlusion element 28 for separation of blood inflow and outflow. By placing occlusion element 28 between distal end 21 of supply elongated element 20 and exit port 24, only the blood proximal to occlusion element 28 enters supply lumen 120, and the thermally altered blood only reaches that part of the arterial system which is distal to occlusion element 28.

Figure 2:
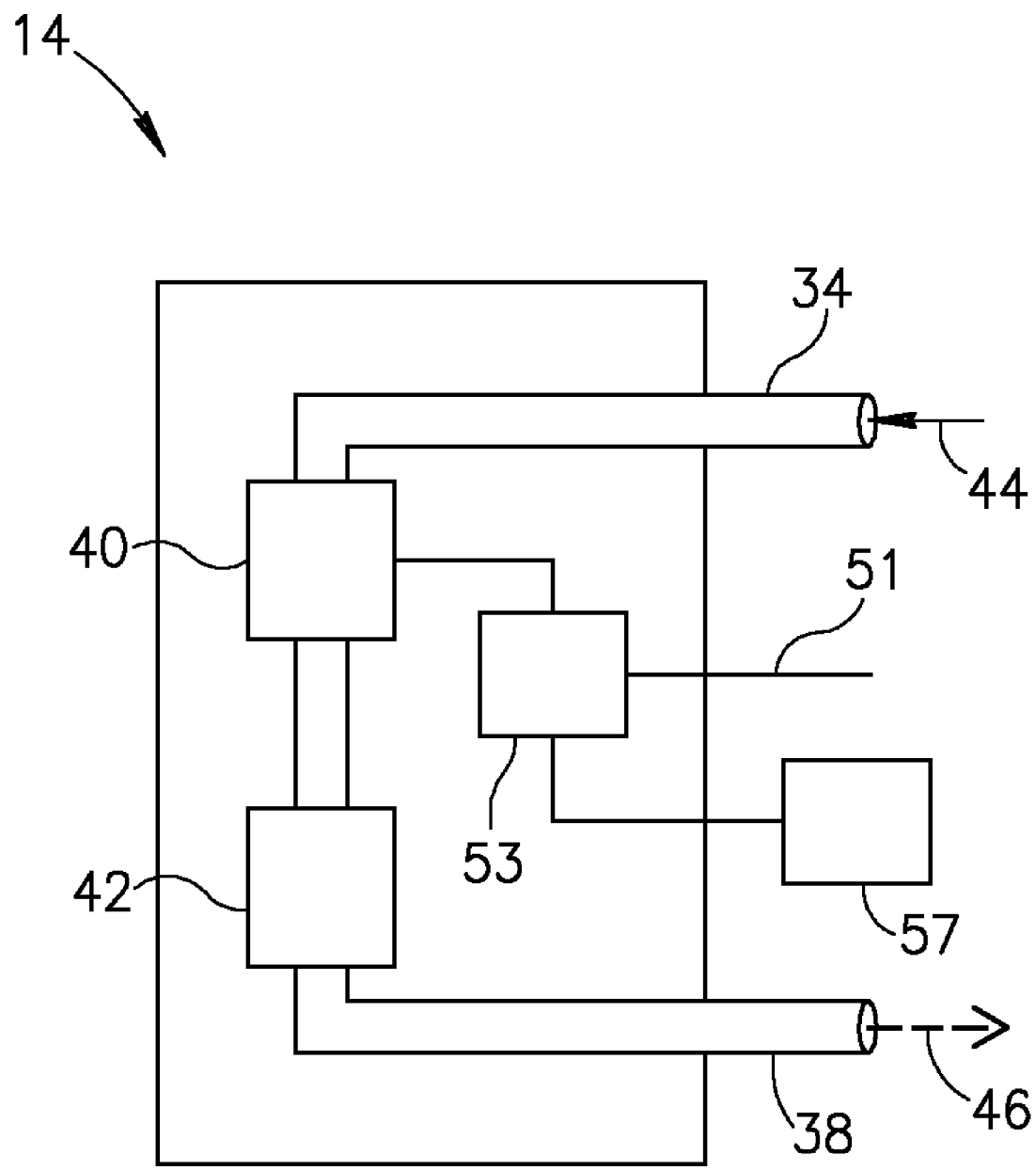
FIG. 2 is a schematic illustration of the control unit of the systems of FIGS. 1A and 1B.

Reference is now made to FIG. 2, which is a schematic illustration of control unit 14 in greater detail. Control unit 14 includes supply blood inlet 34 for receiving normothermic blood, depicted by unbroken arrow 44, and delivery blood outlet 38 for delivering thermally altered blood, depicted by broken arrow 46. Control unit 14 further includes a thermal adjustor 40 for changing a temperature of normothermic blood received from supply blood inlet 34, thus producing thermally altered blood. Thermal adjustor 40 can be a heating mechanism, a cooling mechanism, or a combination heating/cooling mechanism which is controllable by a user. In a preferred embodiment, thermal adjustor 40 is a cooling mechanism such as, for example, Medtronic, Inc.'s Bio-Cal® Blood Temperature Control Module or the MYOthermXP® Cardioplegia System. Alternatively, thermal adjustor 40 comprises a coiled tubing in an ice bath. In a preferred embodiment, control unit 14 further includes a pumping mechanism 42 to facilitate delivery of thermally altered blood through delivery blood outlet 38. Pumping mechanism 42 can be, for example, a centrifugal blood pump (Bio-Pump®, Medtronic, Inc.; Sarns™ Centrifugal System, Terumo Cardiovascular Systems) or an electromagnetic pump (Levitronix® CentriMag® Blood Pumping System, Levitronix GmbH). In one embodiment, control unit 14 further comprises a vacuum to assist in withdrawal of the normothermic blood.

In order to more closely monitor physiological parameters during a procedure, sensors 50 may be placed at or near exit port 24, shown schematically in FIGS. 1A and 1B. Sensors 50 can include one or several sensors, capable of measuring pressure, temperature, flow, or a combination thereof. In an alternative embodiment, pressure is measured by providing an additional lumen referred to as a pressure lumen. The pressure lumen has a proximal pressure transducer attached thereto which is capable of measuring the pressure of a column of fluid located within the pressure lumen. Sensors 50 are in communication with control unit 14 via conventional wires 51 or via wireless communication. As shown in FIG. 2, control unit 14 can further include a processor 53 for receiving and processing signals from sensors 50 and providing an output based on the processed signals. Output can be sent to a display 57, which provides output information to a user. The user can make a decision based on this output information regarding further adjustments of the temperature, flow and pressure. Display 57 can be, for example, a visual, audio, numeric or any other suitable display. When a user sees the display, he/she can manually adjust thermal adjustor 40. The user can also decide to immediately stop the procedure if necessary. Alternatively, processor 53 sends output directly to thermal adjustor 40, which then automatically changes cooling or heating parameters based on the output.

In one embodiment, hub 30 further includes an infusion port 52, as shown in FIGS. 1A and 1B. Infusion port 52 can be used, for example, to introduce contrast media to the site. Alternatively, infusion port 52 can be used to introduce drugs. For example, lytic agents which are typically used to dissolve clots can be introduced via infusion port 52 into an artery, rather than the common practice of intravenous delivery of these agents. Alternatively, in some circumstances it may be desirable to introduce clotting agents, which can be done via infusion port 52. It should be readily apparent that any suitable agent, compound, drug, or substance can be introduced via infusion port 52, and all of these possibilities are included within the scope of the present invention.

Occlusion element 28 is comprised of an a traumatic surface so as not to damage the inner walls of a blood vessel. In a preferred embodiment, occlusion element 28 has a hydrophilic surface, which by attracting water forms a natural a traumatic layer. Furthermore, a hydrophilic surface can provide means for occlusion which is configured to open when in contact with water components from the blood. Occlusion element 28 may further include a coating for providing long-term (measured in hours, days or even months) implantation of catheter 12 in the body. Alternatively or in addition, occlusion element 28 may further include a drug coating. In one embodiment, occlusion element 28 is a balloon, such as is commonly used with catheter systems, and is expandable by introduction of a fluid therein, wherein the fluid can be a liquid or a gas. In this embodiment, a separate inflation lumen is included within catheter 12, either alongside or coaxial with delivery elongated element 22, and is in fluid communication with occlusion element 28. Fluid is introduced via an inflation port (not shown) positioned at hub 30. These types of balloons and inflation lumens are commonly known in the art. The balloon may be elastomeric, compliant, semi-compliant or non-compliant, as long as it serves to occlude the vessel without causing damage to the internal walls. In one embodiment, the balloon is pre-formed and relatively thin, so as to reduce the pressure necessary to inflate the balloon, while keeping the outer diameter to a minimum. For example, balloon thickness may range from 0.0001 inches to 0.001 inches, a range which is smaller than thicknesses of standard occlusion balloons.

In another embodiment, occlusion element 28 is a self-expanding element confined within a retractable sheath, such that upon retraction of the sheath, the self expanding element expands to a diameter sufficient to occlude the vessel. In this embodiment, the sheath is connected to a retractor positioned at proximal end 16 of catheter 12. The self-expanding element may be comprised of an elastic or spring-like material, or a shape-memory alloy. Such materials are known in the art. In another embodiment, occlusion element 28 is a mechanically actuated mechanism, whereby it is expanded by mechanical means. In yet another embodiment, occlusion element 28 is comprised of a temperature sensitive material which can be expanded or retracted by exposure to specific temperatures. Specifically, perfusion of cooled or heated blood through delivery lumen 122 would cause expansion of occlusion element 28, and perfusion of normothermic blood through delivery lumen 122 (such as, for example, during renormalization of temperature) would cause retraction of occlusion element 28. This may be accomplished, for example, by using a shape-memory material, either as occlusion element 28 itself, or as an actuator positioned alongside occlusion element 28. Similarly, this could be accomplished by using a bi-metallic strip. In one embodiment, occlusion element 28 is an integral part of the catheter, wherein a portion of catheter 12 having a slightly wider diameter is configured to be wedged into the vessel, and thus acts as occlusion element 28, providing both occlusion and anchoring functionality.

Occlusion element 28 further includes a radiopaque marker 48 for viewing of a location of catheter 12 generally and occlusion element 28 specifically within the vessel. In one embodiment, occlusion element 28 is itself comprised of radiopaque material. In alternative embodiments, one or more radiopaque markers 48 are positioned on occlusion element 28. Additional radiopaque markers 48 may also be positioned in other places along catheter 12 such as, for example, at distal end 18, or at inlet ports 26. In one embodiment, a radiopaque marker 48 is positioned at the distal tip of catheter 12. Radiopaque marker 48 can be a ring surrounding the distal tip, or, in order to minimize stiffness at the tip, a radiopaque marker 49 (shown in FIG. 1B) may be comprised of a small sliver of radiopaque material embedded within a portion of the distal tip. In one embodiment, radiopaque marker 48 is filled with an adhesive and positioned so as to seal an inflation lumen for inflation of occlusion element 28.

Figure 3:
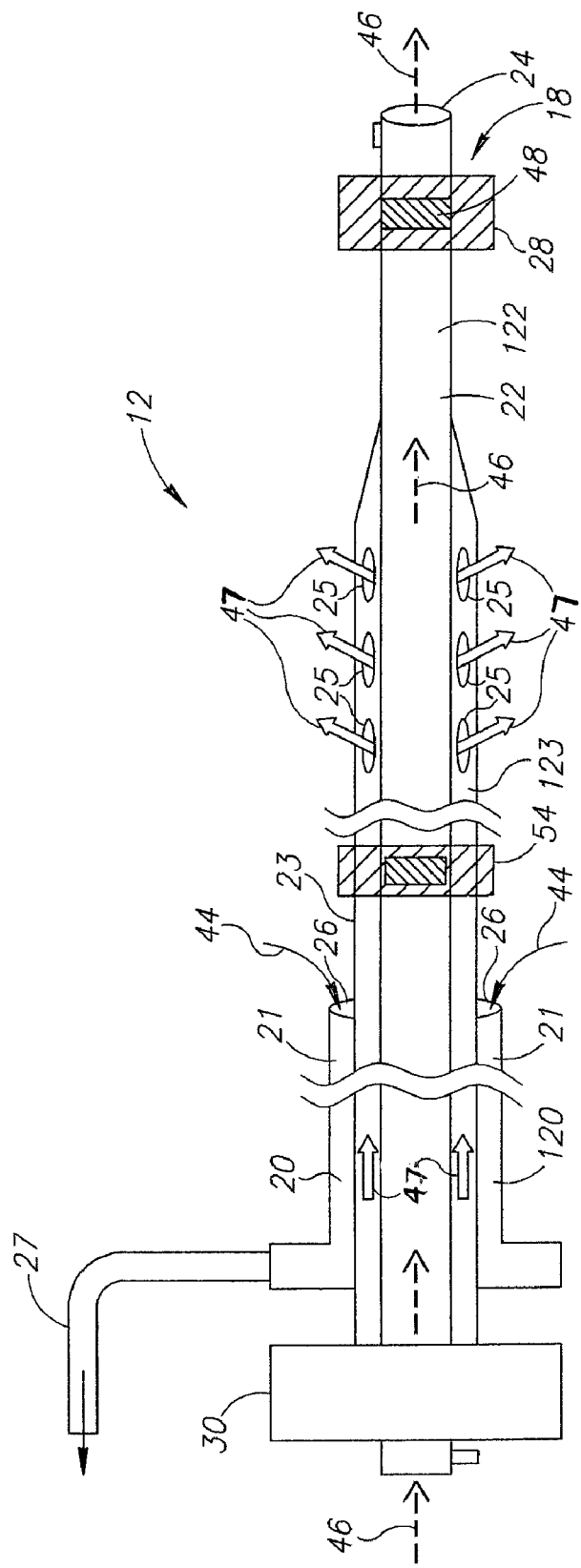
FIG. 3 is an illustration of a catheter in accordance with another embodiment of the present invention.

Reference is now made to FIG. 3, which is an illustration of a catheter 12 in accordance with another embodiment of the present invention. Catheter 12 is similar in construction to catheter 12 shown in FIGS. 1A and 1B, with an additional feature of an auxiliary delivery elongated element 23, preferably situated between supply elongated element 20 and delivery elongated element 22. Auxiliary delivery elongated element 23 is preferably an elongated tubular member having an auxiliary lumen 123 therethrough, and is configured to receive a supplemental blood flow from control unit 14 (shown in FIGS. 1A and 1B) and to deliver the supplemental blood (depicted by wide arrows 47) to a vessel. In one embodiment, the supplemental blood is taken from the control unit 14 and introduced into auxiliary delivery elongated element 23 at an initial thermally altered temperature. Supplemental blood as depicted by wide arrows 47 undergoes a temperature change during its flow from the proximal end to the distal end of auxiliary delivery elongated element due to conduction from the normothermic blood in the blood vessel which is in close proximity thereto. In this embodiment, the temperature of supplemental blood that exits ports 25 of auxiliary delivery elongated element 23 is of a different temperature $T_2$ than the temperature $T_1$ of the thermally altered blood depicted by broken arrows 46, which is delivered to the target site. The presence of an additional layer of blood flow in a lumen surrounding delivery elongated element 22 provides increased insulation for the thermally altered blood being delivered to the target site.

Furthermore, blood from auxiliary delivery elongated element 23 can be used for simultaneous treatment of different parts of the body. Thus, for example, if it were desired to treat the target site with one temperature and an additional site with another temperature, auxiliary delivery elongated element 23 could be used for treatment of the additional site. The amount of temperature change that occurs within auxiliary delivery lumen 123 depends on the flow rate and the initial temperature difference between the thermally altered blood entering auxiliary delivery lumen 123 and the normothermic blood surrounding auxiliary delivery elongated element 23.

In a preferred embodiment, auxiliary delivery elongated element 23 is coaxially arranged with respect to delivery elongated element 22, and includes at least one secondary exit port 25, preferably in a distal portion thereof. In an alternative embodiment, exit port 25 is configured similar to inlet port 26 as depicted in FIG. 1B, wherein an exit port 25 is created by the coaxial arrangement of auxiliary delivery elongated element 23 and delivery elongated element 22, wherein an inner diameter of auxiliary delivery elongated element 23 is sized at least 0.1 mm greater than an outer diameter of delivery elongated element 22. The space created by this difference in diameter is sufficient for delivering supply blood to the vessel. The distal portion of auxiliary delivery elongated element 23 is proximal to exit port 24. Supply elongated element 20 is positioned coaxially with respect to auxiliary delivery elongated element 23, and distal end 21 of supply elongated element 20 is proximal to secondary exit ports 25. In one embodiment, supply elongated element 20 is a standard vascular sheath and may have a side arm 27 from which normothermic blood is sent to control unit 14. In another embodiment, supply elongated element 20 is an extended sheath, and may extend to 100 cm or more depending on the application.

A second occlusion element 54 may be positioned proximal to secondary exit ports 25 and distal to inlet ports 26 of supply elongated element 20. In this way, a first target site is supplied by thermally altered blood exiting delivery elongated element 22 and having a temperature $T_1$, and a second target site is separately supplied by supplemental blood exiting auxiliary delivery elongated element 23 and having a temperature $T_2$.

Figure 4A:
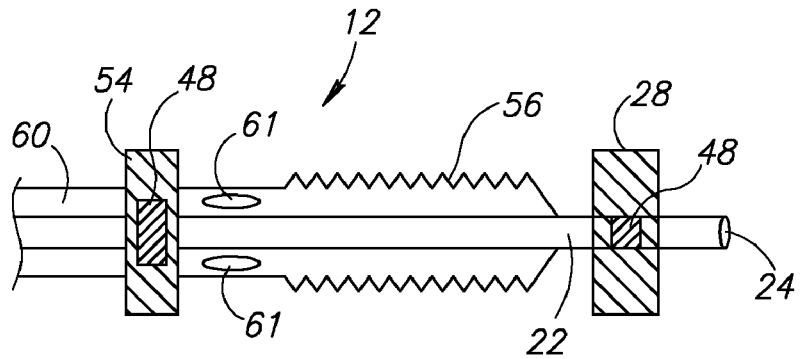
FIGS. 4A, 4B and 4C are illustrations of several embodiments of a distal portion of the catheters of FIG. 1A, FIG. 1B and FIG. 3, having distal ends which are variably positionable.
Figure 4B:
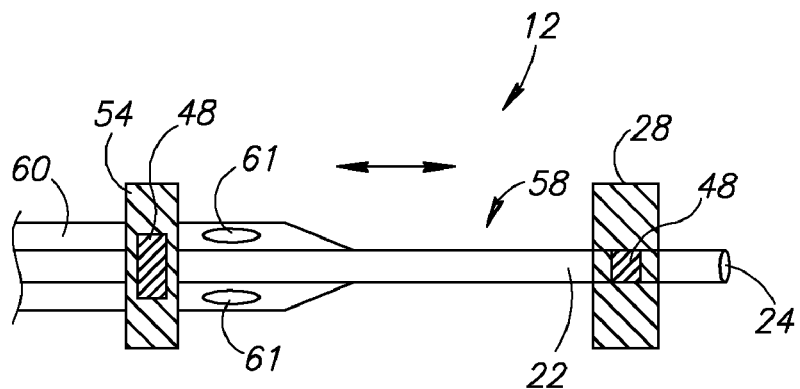
Figure 4C:
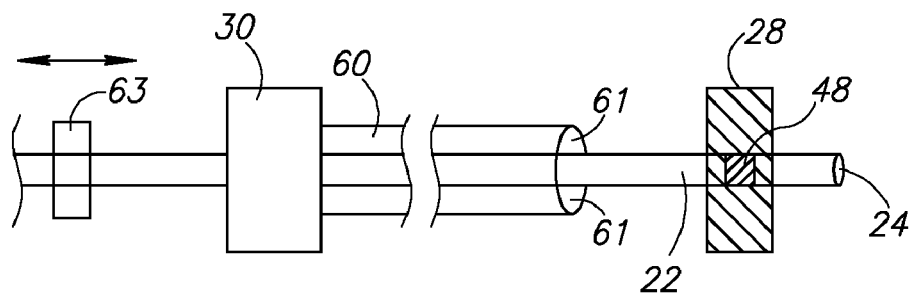

Reference is now made to FIGS. 4A-4C, which are illustrations of a distal portion of catheter 12, in accordance with another embodiment of the present invention, wherein exit port 24 is positionable at varying distances from ports 61. Ports 61 are inlet or outlet ports of a coaxial elongated element 60, which can be any elongated element coaxial to delivery elongated element 22. In one embodiment, coaxial elongated element 60 is a supply elongated element and ports 61 are inlet ports. In another embodiment, coaxial elongated element 60 is an auxiliary delivery elongated element, and ports 61 are secondary exit ports. Delivery elongated element 22 is movable within coaxial elongated element 60. Movement can be a twisting motion, for example, wherein delivery elongated element 22 and coaxial elongated element 60 are attached with a bellows 56, as shown in FIG. 4A. Alternatively, movement can be a sliding motion, wherein delivery elongated element 22 and coaxial elongated element 60 are attached via telescoping means 58, as shown in FIG. 4B. In a preferred embodiment, movement is achieved by coaxial arrangement of coaxial elongated element 60 and delivery elongated element 22, as shown in FIG. 4C. In this arrangement, delivery elongated element 22 can be variably positioned within coaxial elongated element 20. Thus, a length of delivery elongated element 22 may protrude proximal to the proximal end of catheter 12. In this case, it may be necessary to include an adjustable anchor 63 for anchoring the proximal portion of delivery elongated element 22 to the body or surgical drape of the patient. Alternatively, a length of supply elongated element 20 may protrude proximal to the proximal end of catheter 12. In this case, it may be necessary to include an adjustable anchor for anchoring the proximal portion of supply elongated element 20 to the body or surgical drape of the patient. These configurations allow for the tip of catheter 12 to be positioned as desired, without concern for the resulting location of the proximal end. Any suitable adjustable anchor means may be used, including, for example, a luer lock, a gland, a squeeze-lock mechanism, etc. Any other means for changing a distance between exit port 24 and ports 61 is included within the scope of the invention.

Figure 5A:
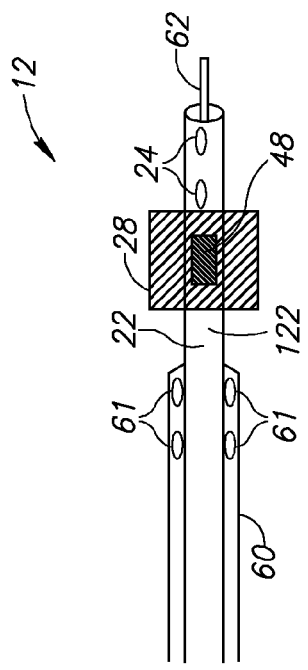
FIGS. 5A-5C are illustrations of a catheter having a bendable distal end, in accordance with one embodiment of the present invention.
Figure 5B:
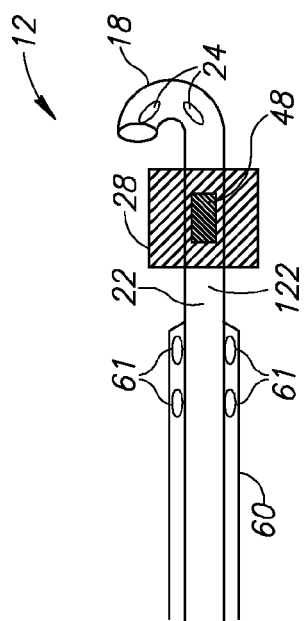
Figure 5C:
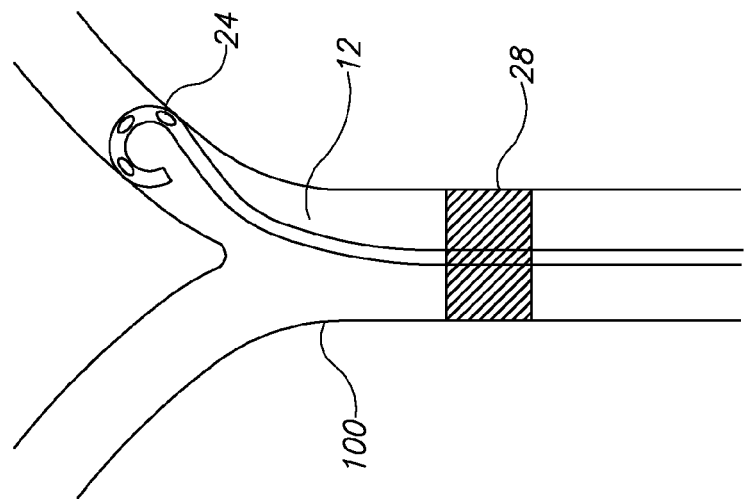

In some instances, it may be desirable to anchor catheter 12 into a vessel, providing greater control and easier accessibility to the target site. Reference is now made to FIGS. 5A-5C, which are illustrations of a catheter having a bendable distal end 18 for anchoring. As shown in FIG. 5A, catheter 12 includes delivery elongated element 22 and occlusion element 28. At least one exit port 24 is located distal to occlusion element 28. In one embodiment, exit port 24 is at distal end 18 of catheter 12. In another embodiment, exit port 24 is located anywhere between occlusion element 28 and distal end 18. In one embodiment, distal end 18 is initially in a straightened positioned as it is advanced over a guidewire 62. Guidewire 62 is insertable through delivery lumen 122. Alternatively, guidewire 62 may be insertable through a separate guidewire lumen (not shown), which is either coaxial with or adjacent to delivery lumen 122. Catheter 12 is advanced over guidewire 62 until a desired location is reached. Guidewire 62 is then removed, allowing catheter 12 to assume a bent configuration, as depicted in FIG. 5B. The bent configuration is suitable for anchoring in a vessel, as shown schematically in FIG. 5C. In an alternative embodiment, catheter 12 has a fixed wire at its distal end, and distal end 18 is initially straightened by inserting a removable stylet. Once the desired location is reached, the stylet is removed, causing distal end 18 to assume its bent configuration. In one embodiment, distal end 18 is comprised of a shape memory alloy.

Alternatively, it may be desirable to anchor catheter 12 in a vessel other than the one leading to the target site. For example, if catheter 12 is anchored in a branch vessel, thermally altered blood can be diverted into the main vessel by strategically placing exit port 24 at a specific location or locations.

Figure 6:
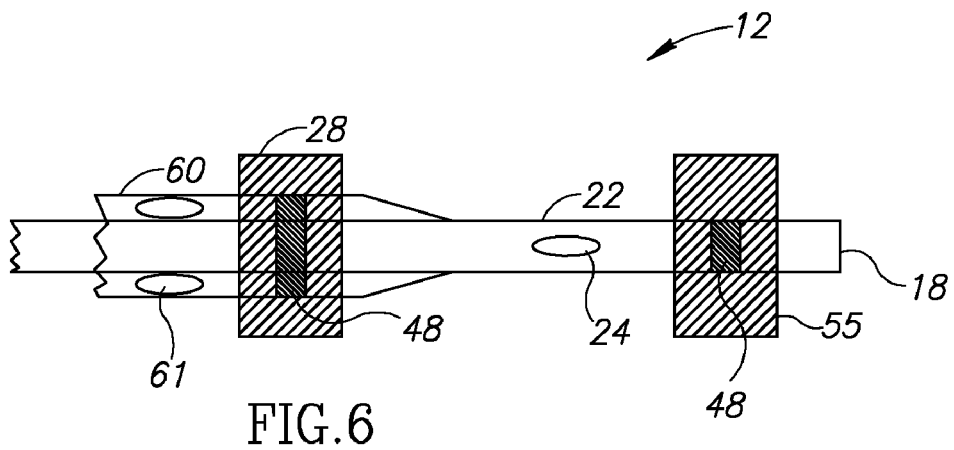
FIG. 6 is an illustration of a catheter which is suitable for anchoring in a separate vessel in accordance with one embodiment of the present invention.

Reference is now made to FIG. 6, which is an illustration of catheter 12 suitable for anchoring in a separate vessel, in accordance with one embodiment of the present invention. Catheter 12 has a closed distal end 18 and an exit port 24 located along its shaft, proximal to distal end 18. Catheter 12 further includes at least two occlusion elements: first occlusion element 28, which is positioned between exit port 24 and ports 61 of coaxial elongated element 60, and distal occlusion element 55, which is positioned between exit port 24 and distal end 18 of catheter 12. Coaxial elongated element 60 and ports 61 can be supply elongated element 20 with inlet ports 26, or auxiliary delivery elongated element 23 and secondary exit ports 25. First occlusion element 28 is designed to separate an area for receiving thermally altered blood (i.e. the target site) from an area supplying normothermic blood to control unit 14, or from an area receiving supplemental blood at a different temperature $T_2$. Distal occlusion element 55 is designed to act as an anchor, while also separating an area for receiving thermally altered blood (the target site) from an untreated area. In a preferred embodiment, first and distal occlusion elements 28 and 55 include radiopaque markers 48 for allowing for positioning of catheter 12 within the blood vessel.

Figure 7A:
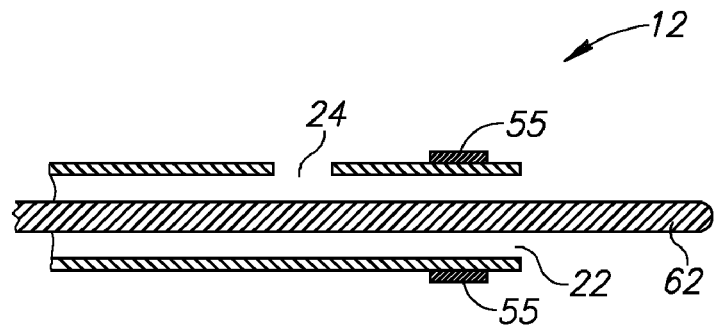
FIGS. 7A-7C are illustrations of a distal portion of a catheter which is suitable for anchoring in a separate vessel, in accordance with another embodiment of the present invention.
Figure 7B:
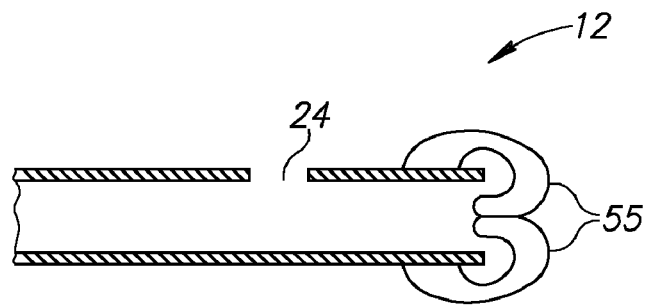
Figure 7C:
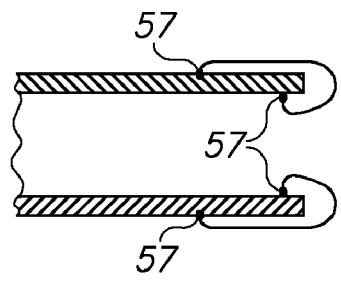

Reference is now made to FIGS. 7A and 7B, which are illustrations of a distal portion of catheter 12, suitable for anchoring in a separate vessel, in accordance with another embodiment of the present invention. As shown in FIG. 7A, guidewire 62 is introducible through delivery elongated element 22. In an alternative embodiment, catheter 12 includes a separate guidewire elongated element (not shown) either coaxial with or alongside delivery elongated element 22. Catheter 12 includes a distal occlusion element 55, which in one embodiment is an inflatable balloon designed to extend over distal end 18 upon inflation. As shown in FIG. 7B, inflation of distal occlusion element 55 results in expansion of the balloon over distal end 18, causing the delivery lumen to be sealed. This type of configuration can be accomplished, for example, by attaching the balloon to the catheter shaft near the distal end of the catheter, such that upon inflation, the balloon is configured to expand over the edge of catheter 12. Alternatively, distal occlusion element 55 can have multiple attachment points 57, as shown in FIG. 7C in a deflated state, which dictate a direction of expansion for distal occlusion element 55. Exit port 24 is located on the shaft of catheter 12, and is positioned proximal to distal occlusion element 55.

It should be readily apparent that in all of the described embodiments, additional lumens may be included for various purposes. For example, a lumen for oxygenation of blood may be added. Additional cooling/heating lumens or additional lumens to control flow or pressure may be added as well.

In a preferred embodiment, system 10 is used to provide hypothermia for treatment of stroke. A target temperature for cooling is in the range of 18 to 30 degrees Celsius, and may be maintained for hours or days. The system described herein also allows for gradual rewarming of the treated area by slowly introducing blood of different temperatures.

Figure 8C:
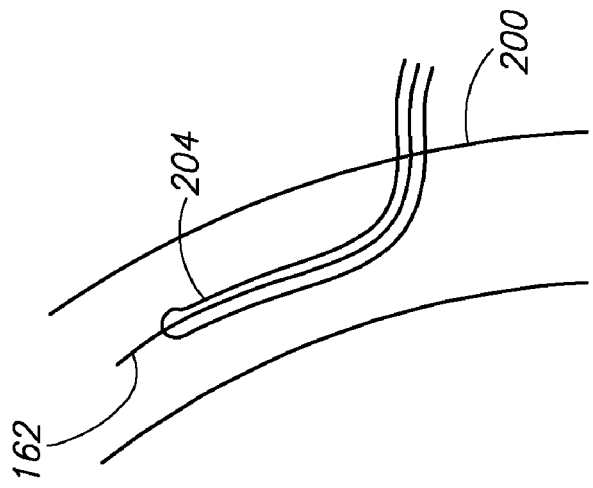
FIGS. 8A-8H are illustrations of the steps of a method of positioning a catheter in a vessel in accordance with embodiments of the present invention.
Figure 8B:
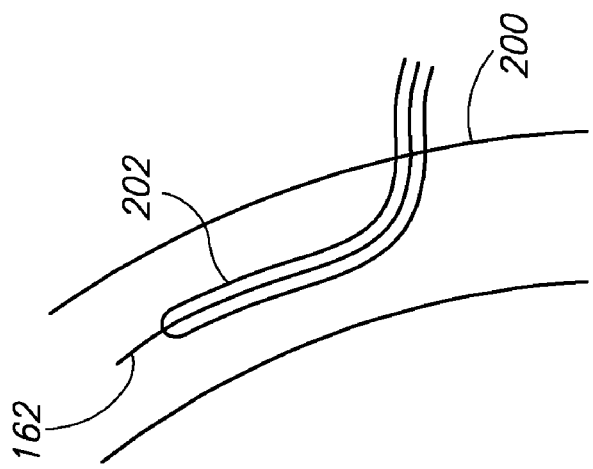
Figure 8A:
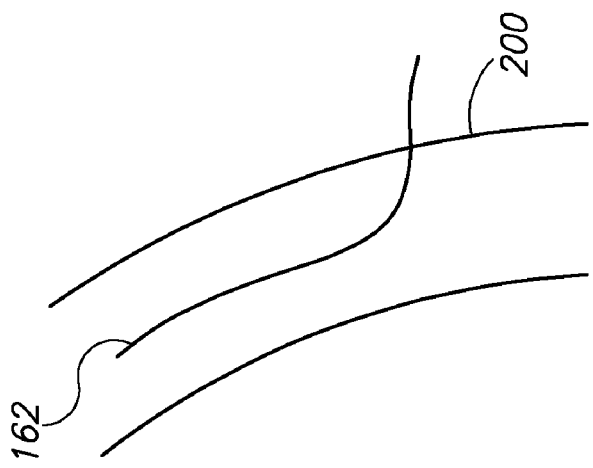
Figure 8F:
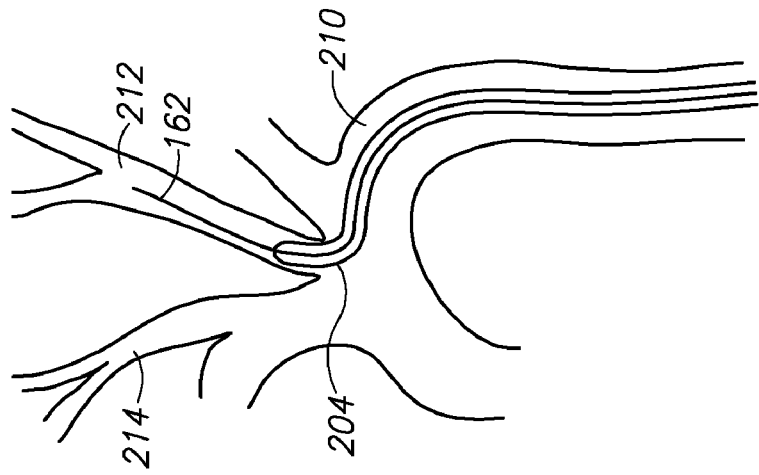
Figure 8E:
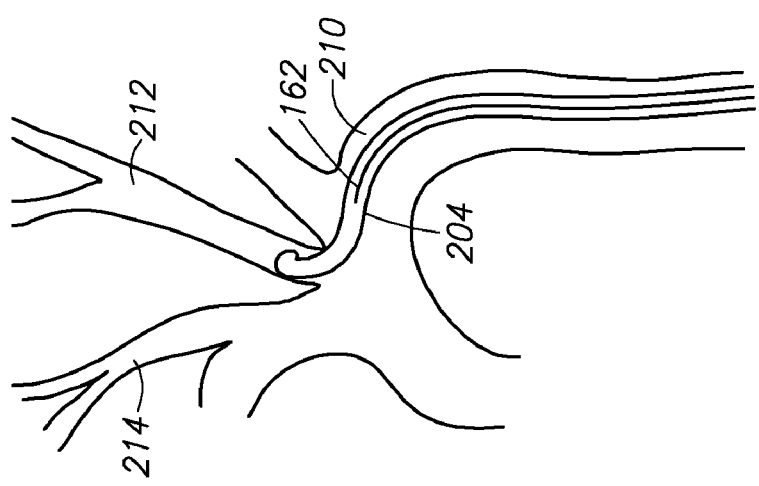
Figure 8D:
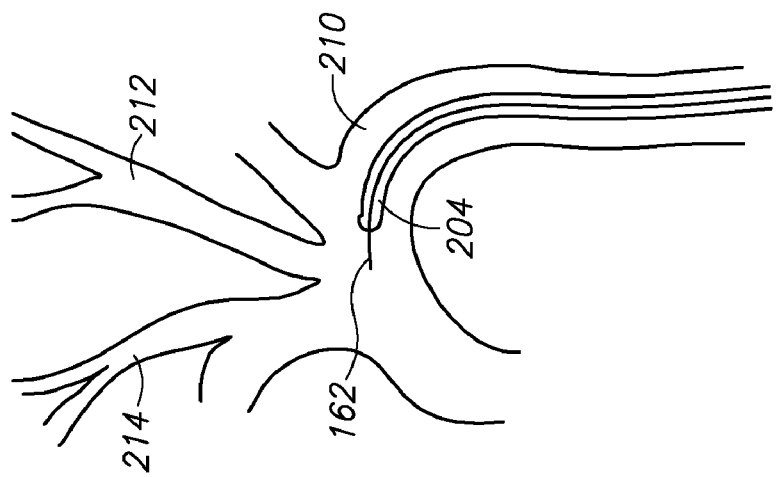
Figure 8H:
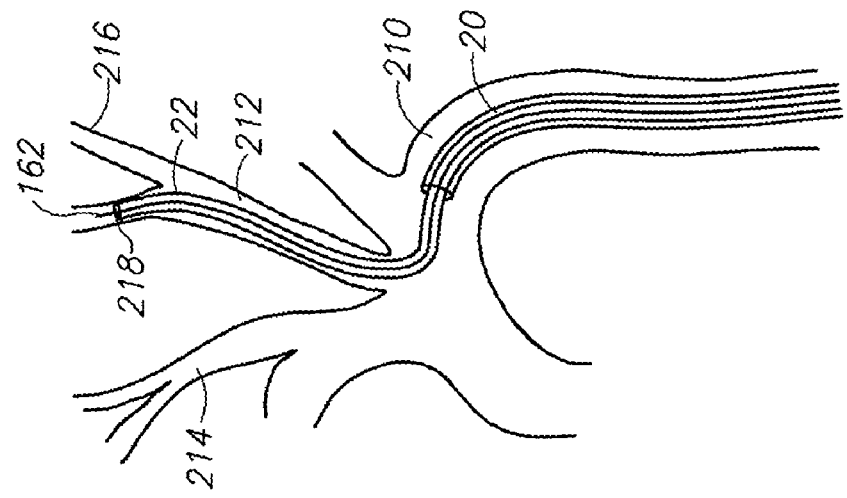
Figure 8G:
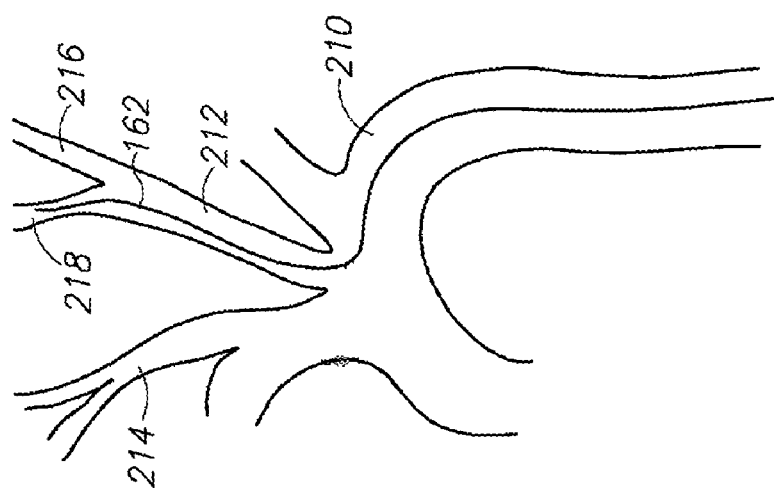

Introduction and positioning of catheter 12 into a selected vessel in the body can be accomplished in various ways. Reference is now made to FIGS. 8A-8H, which are schematic illustrations of a method of positioning catheter 12 in a selected vessel in the body. In the embodiment shown, catheter 12 is positioned in the left internal carotid artery. However, it should be readily apparent that catheter 12 may alternatively be positioned in the right or left common carotid arteries, or any of the internal or external carotid arteries based on the target location. Initially, an incision or puncture is made at a peripheral location, typically the femoral artery, although other locations such as the brachial or radial artery, for example, can be used as well. A guidewire 162 is inserted through the incision and into the vessel, in this case, femoral artery 200, as shown in FIG. 8A. Optionally, as shown in FIG. 8B, a vascular sheath 202 with a dilator portion is introduced over guidewire 162. Vascular sheaths and dilators are commonly known in the art, and are commonly used for providing vascular access to catheters. Once the sheath is in place, the dilator is removed, and a search catheter 204 is introduced over guidewire 162, as shown in FIG. 8C. Search catheter 204 can be, for example, a guiding catheter or an angiography catheter, both of which are types of catheters known in the art, and which include a tip which is pre-shaped in various configurations, suitable for selecting particular vessels. While search catheter 204 is positioned over guidewire 162, the tip of search catheter 204 is relatively straight. Search catheter 204 and guidewire 162 are advanced together through arterial system and into the aortic arch 210, as shown in FIG. 8D. Guidewire 162 is pulled back proximally, which allows for search catheter 204 to assume its bent configuration, suitable for selecting a specific vessel. Search catheter 204 is then used to locate the left common carotid artery 212, as shown in FIG. 8E. Search catheter 204 may alternatively be used to locate the right common carotid artery 214. Guidewire 162 is then advanced into left common carotid artery 212, as shown in FIG. 8F. Search catheter 204 is removed, and guidewire 162 may be advanced further into the left internal carotid artery 218, as shown in FIG. 8G. Alternatively, guidewire 162 may be advanced into an external carotid artery 216, or may remain in the common carotid artery 212, depending on the targeted area. Catheter 12 of the present invention is then introduced over guidewire 162, with the tip of delivery elongated element 22 positioned within the selected vessel, in this case left internal carotid artery 218 as shown in FIG. 8H. Supply elongated element 20 preferably remains within aortic arch 210. This method can be used for a catheter 12 in accordance with any of the described embodiments above.

Figure 9C:
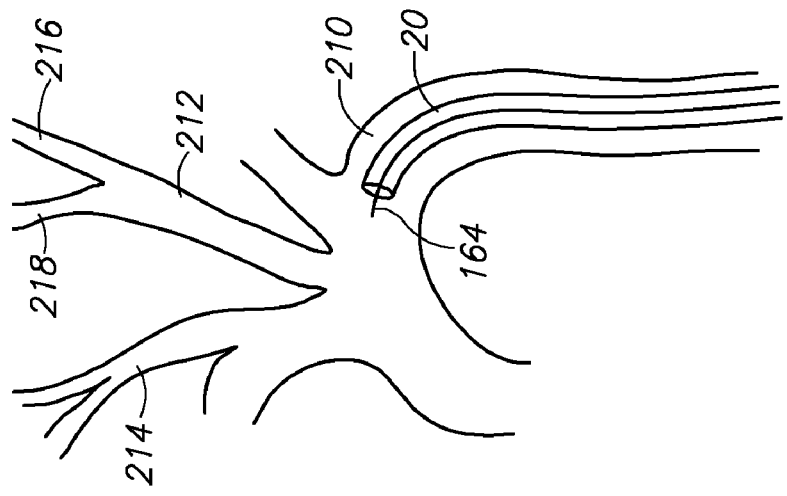
Figure 9B:
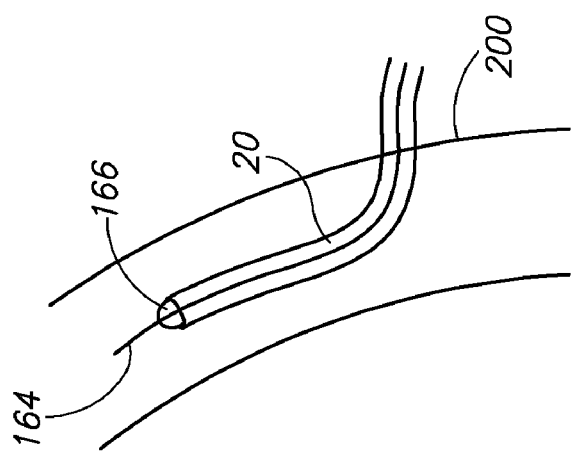
Figure 9A:
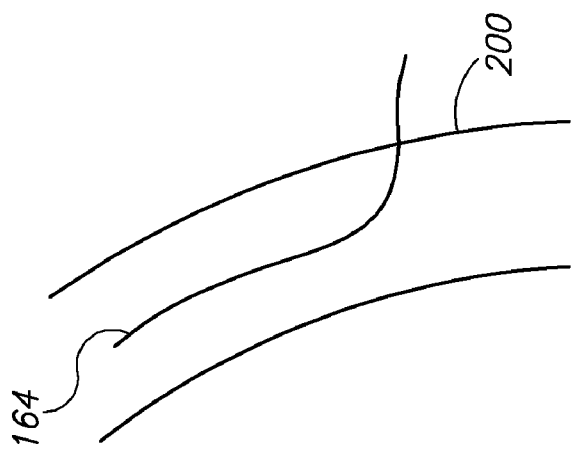
Figure 9H:
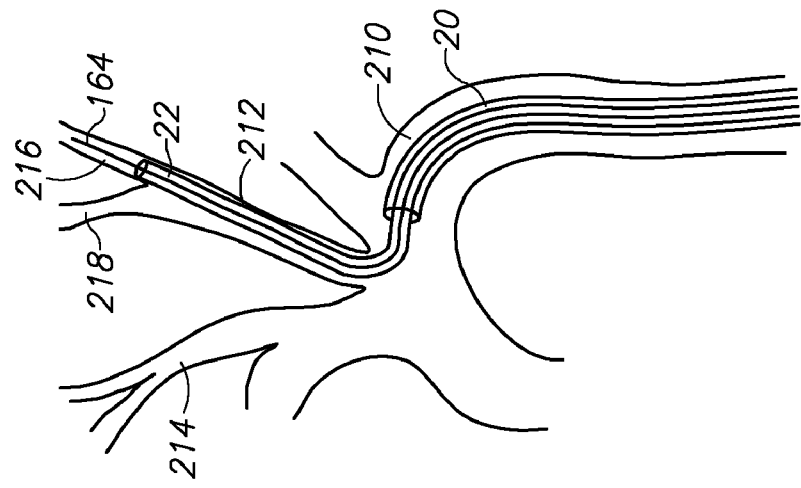
Figure 9G:
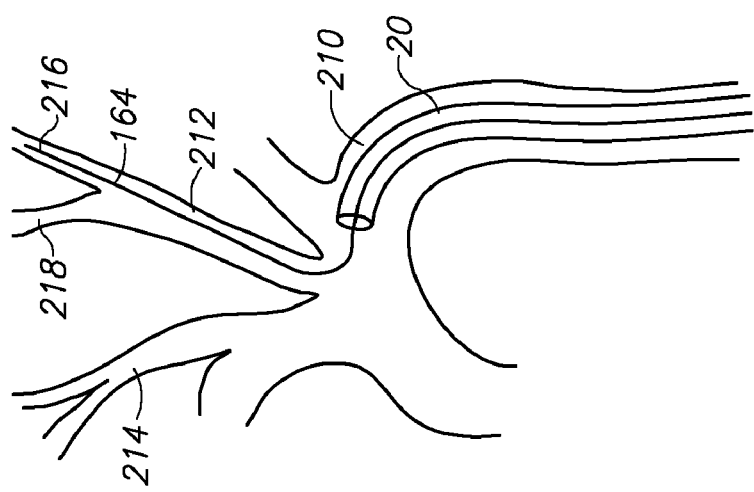

Reference is now made to FIGS. 9A-9H, which are schematic illustrations of the steps of an alternative method of introduction and positioning of catheter 12 into a selected vessel in the body. In this method, an incision or puncture is made as described above, and a long guidewire 164 is introduced into the vessel, in this case, femoral artery 200, as shown in FIG. 9A. Supply elongated element 20, which in at least one embodiment described above (see for example, FIG. 1B) is detachable from the rest of catheter 12, is introduced over guidewire 164, as shown in FIG. 9B. A removable dilator 166 is positioned within supply elongated element 20 to facilitate percutaneous introduction. Supply elongated element 20 is advanced, either with the removable dilator in place or after the removable dilator has been removed, until supply elongated element 20 is in a position within aortic arch 210 proximal to the left common carotid artery 212, as shown in FIG. 9C. If the dilator had not previously been removed, at this point the dilator is removed. Search catheter 204 is then introduced through supply elongated element 20, as shown in FIG. 9D. Guidewire 164 is pulled back proximally, which allows for search catheter 204 to assume its bent configuration, suitable for selecting a specific vessel. Search catheter 204 is then used to locate the left common carotid artery 212, as shown in FIG. 9E. Search catheter 204 may alternatively be used to locate the right common carotid artery 214. Guidewire 164 is then advanced into left common carotid artery 212, as shown in FIG. 9F. Search catheter 204 is removed, and guidewire 164 may be advanced further into the left external carotid artery 216, as shown in FIG. 9G. Alternatively, guidewire 164 may be advanced into an internal carotid artery 218, or may remain in the common carotid artery 212, depending on the desired target. Remaining portions of catheter 12 which are not yet in the vessel are then introduced over guidewire 164, with the tip of delivery elongated element 22 positioned within the selected vessel, in this case left external carotid artery 216. Supply elongated element 20 preferably remains within aortic arch 210. This last step creates assembly of catheter 12 within the desired location.

Figure 10C:
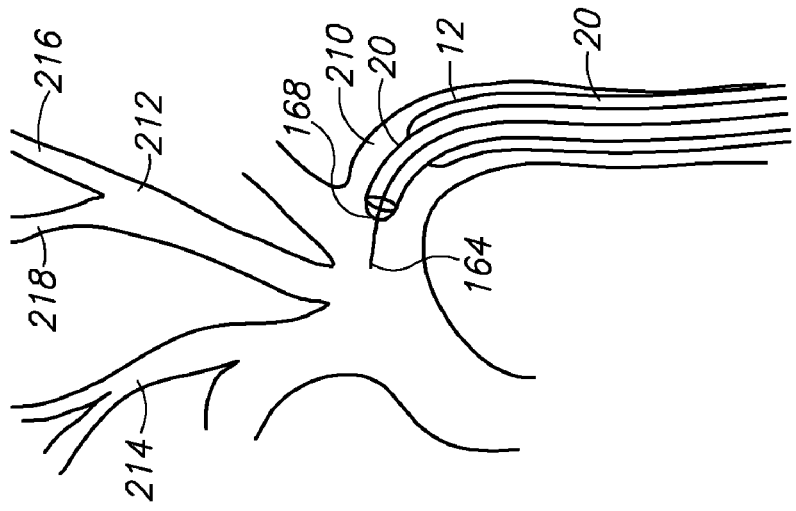
FIGS. 10A-10F are illustrations of the steps of a method of positioning a catheter in a vessel in accordance with yet additional embodiments of the present invention.
Figure 10B:
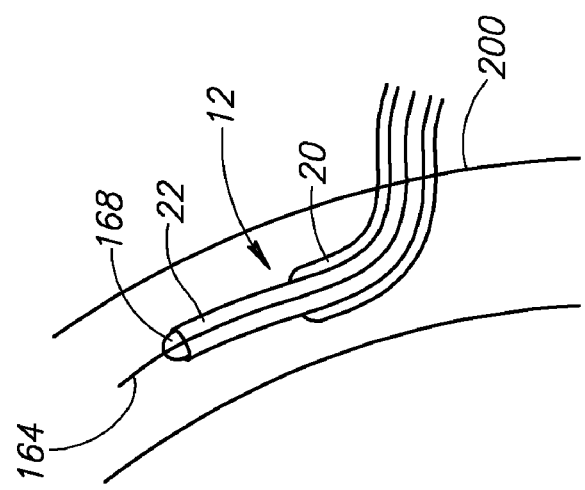
Figure 10A:
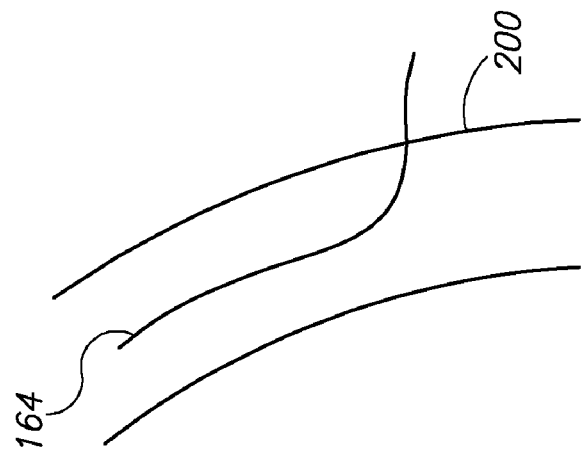
Figure 10F:
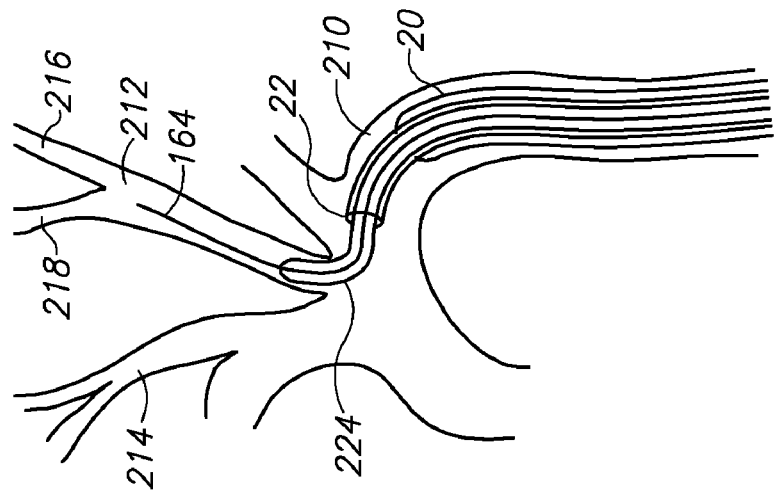
Figure 10E:
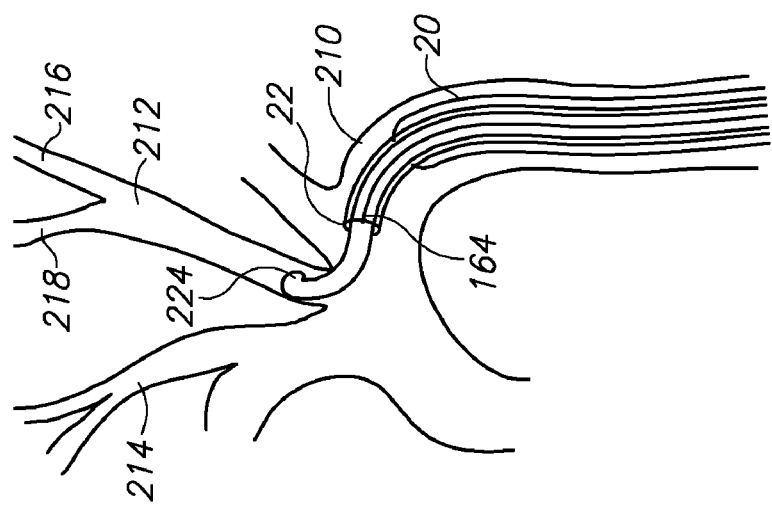
Figure 10D:
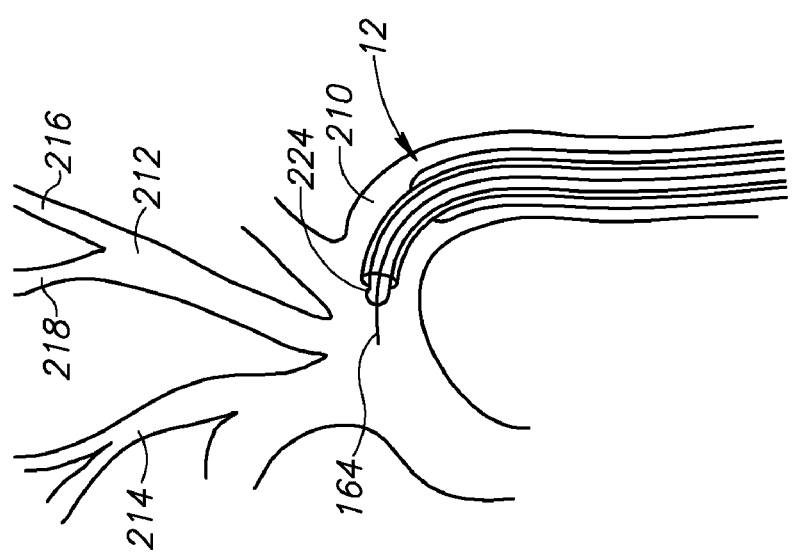

Reference is now made to FIGS. 10A-10F which are schematic illustrations of the steps of an alternative method of introduction and positioning of catheter 12 into a selected vessel in the body. In this embodiment, an incision or puncture is made as described above, and a long guidewire 164 is introduced into the vessel, as shown in FIG. 10A. A dilator 168 is positioned within delivery elongated element 22, and catheter 12 with dilator 168 in place is advanced over guidewire 164, as shown in FIG. 10B. Catheter 12 and dilator 168 are advanced over guidewire 164 into aortic arch 210, as shown in FIG. 10C. When catheter 12 is in position in aortic arch 210, dilator 168 is removed, and a search catheter 224 may then be introduced though delivery elongated element 22, as shown in FIG. 10D. Search catheter 224 is sized to fit within delivery elongated element 22. Alternatively, delivery elongated element 22 may itself be configured with a bent configuration for selecting a vessel, and thus may be used as a search catheter. Guidewire 164 is pulled back proximally, and search catheter 224 or bent delivery elongated element 22 is used to locate the left common carotid artery 212, as shown in FIG. 10E. Search catheter 224 or bent delivery elongated element 22 may alternatively be used to locate the right common carotid artery 214. Guidewire 164 is then advanced into left common carotid artery 212, as shown in FIG. 10F. Search catheter 224 is removed, and guidewire 164 may be advanced further into the left external carotid artery 216. Alternatively, guidewire 164 may be advanced into an internal carotid artery 218, or may remain in the common carotid artery 212, depending on the targeted area of the brain. Catheter 12 is advanced into left common carotid artery 212, with the tip of delivery elongated element 22 positioned within the selected vessel, in this case left external carotid artery 216. Supply elongated element 20 preferably remains within aortic arch 210. For this embodiment, it may be necessary for supply elongated element 20 to have a tapered distal end so as to avoid damage of the vessel during insertion. If inlet ports are positioned along supply elongated element 20, as in FIG. 1A, the distal end 21 of supply elongated element 20 can be tapered by design. If inlet port 26 is located at the distal end 21 of supply elongated element 20, as shown in FIG. 1B, a temporary tapering element can be included at distal end 21. For example, an inflatable balloon may be positioned at distal end 21 of supply elongated element 20, so that during insertion, the balloon can be inflated, providing a tapered edge, and during collection of supply blood, the balloon can be deflated for blood collection.

In all of the described embodiments, positioning of supply elongated element 20 within the vessel should be such that supply blood is collected from retrograde flow of blood. Thus, it is preferable not to advance the supply elongated element 20 into the common carotid artery. Rather, supply elongated element 20 (or at least the inlet ports 26 from supply elongated element 20) should remain in the aorta. If supply elongated element 20 and delivery elongated element 22 are not detachable from one another, supply elongated element 20 may be sized (lengthwise) so as to avoid its entry into the carotid artery. Alternatively, if supply elongated element 20 and delivery elongated element 22 are detachable, a marker on the distal end of supply elongated element 20 may aid in this positioning. In alternative embodiments, catheter 12 may be placed in other locations in the body depending on the desired target area. For example, a renal artery can be targeted to provide cooling/heating to a kidney, or a coronary artery can be targeted to provide cooling/heating to a heart.

Reference is now made to FIGS. 11A-C, which are illustrations of a method for treating a specific target site in accordance with a preferred embodiment of the present invention. As shown in FIG. 11A, catheter 12 is inserted into a blood vessel, and advanced to a vessel which is in fluid communication with the target site, referred to hereinafter as adjacent vessel 100. In a preferred embodiment, wherein the goal is to selectively cool the brain without induction of systemic hypothermia, the target site is the brain, and vessel 100 is the carotid artery (right or left, common, internal or external). A position of catheter 12 within vessel 100 is monitored by visualization of radiopaque marker 48. When catheter 12 is in the desired location, occlusion element 28 is expanded, as shown in FIG. 11B. This expansion primarily serves to isolate a particular section of adjacent vessel 100 which leads to the target site, thereby preventing normothermal blood from flowing into the target organ, and can also help anchor catheter 12 in place. Reference is now made to FIG. 11C, which illustrates the flow of blood. Once occlusion element 28 is deployed, normothermic blood, represented by arrows 44, enters supply elongated element 20 via inlet ports 26. It should be readily apparent that although the method depicted in FIGS. 11A-11C shows supply elongated element 20 having multiple inlet ports and positioned in a vessel in such a way so as to collect antegrade blood, these depictions should not be regarded as limiting. In alternative embodiments, as described above with reference to FIGS. 1B, 8H and 9H, supply elongated element 20 may have one inlet port, and it may be positioned within the aortic arch. Normothermic blood flows through supply lumen 120, out through inlet connector 32 of hub 30 and through supply blood inlet 34 into control unit 14. Control unit 14 then heats or cools the blood to form thermally altered blood, which is pumped out through delivery blood outlet 38, through outlet connector 36, and into delivery elongated element 22. Thermally altered blood, represented by broken arrow 46, flows out through exit port 24 and into the portion of the blood vessel which leads to the target site. In one embodiment, pharmaceuticals are simultaneously administered to the target site via drug infusion port 52. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application. In a preferred embodiment, the cycle is repeated for 1-72 hours.

Reference is now made to FIGS. 12A-C, which are illustrations of a method for treating a specific target site in accordance with another embodiment of the present invention. As shown in FIG. 12A, catheter 12 is inserted into a blood vessel, and advanced to a vessel which is in fluid communication with the target site, referred to hereinafter as adjacent vessel 100. In a preferred embodiment, wherein the goal is to selectively cool the brain without induction of systemic hypothermia, the target site is the brain, and vessel 100 is the carotid artery (right or left, common, internal or external). A position of catheter 12 within vessel 100 is monitored by visualization of radiopaque marker 48. When catheter 12 is in the desired location, occlusion element 28 and second occlusion element 54 are both expanded, as shown in FIG. 12B. Occlusion element 28 and second occlusion element 54 can be sequentially or simultaneously expanded. Expansion of occlusion element 28 primarily serves to isolate a particular section of blood vessel 100 which leads to the target site, and can also help anchor catheter 12 in place. Expansion of second occlusion element 54 serves to separate an area for delivery of supplemental blood, which is of a different temperature $T_2$ than a temperature $T_1$ of thermally treated blood sent to the target site, and from normothermic blood returning through supply elongated element 20. Reference is now made to FIG. 12C, which illustrates the flow of blood. Once occlusion element 28 and second occlusion element 54 are deployed, normothermic blood, represented by arrows 44, enters supply elongated element 20 via inlet ports 26. It should be readily apparent that although the method depicted in FIGS. 12A-12C shows supply elongated element 20 having multiple inlet ports and positioned in a vessel in such a way so as to collect antegrade blood, these depictions should not be regarded as limiting. In alternative embodiments, as described above with reference to FIGS. 1B, 8H and 9H, supply elongated element 20 may have one inlet port, and it may be positioned within the aortic arch. Normothermic blood flows through supply lumen 120, out through inlet connector 32 of hub 30 and through supply blood inlet 34 into control unit 14. Control unit 14 then heats or cools the blood to form thermally altered blood, which is pumped out through delivery blood outlet 38, through outlet connector 36 and into delivery elongated element 22. Thermally altered blood, represented by broken arrow 46, flows out through exit port 24 and into the portion of the blood vessel which leads to the target site. In addition, supplemental blood, represented by wide arrows 47, is sent through auxiliary delivery elongated element 23 and into a secondary vessel 101, which may lead to a secondary target site. In one embodiment, pharmaceuticals are simultaneously administered to the target site and/or to the supplemental blood via drug infusion port 52. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application.

Figure 13C:
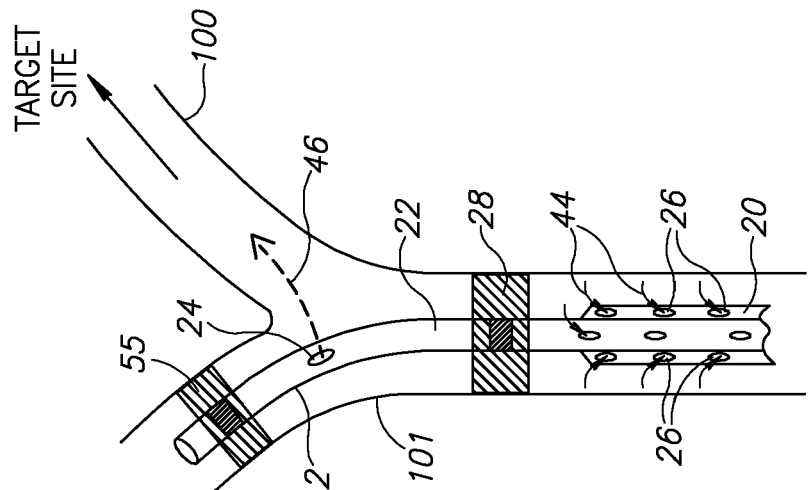
FIGS. 13A-13C are illustrations of a method for treating a specific target site in accordance with yet another embodiment of the present invention.
Figure 13B:
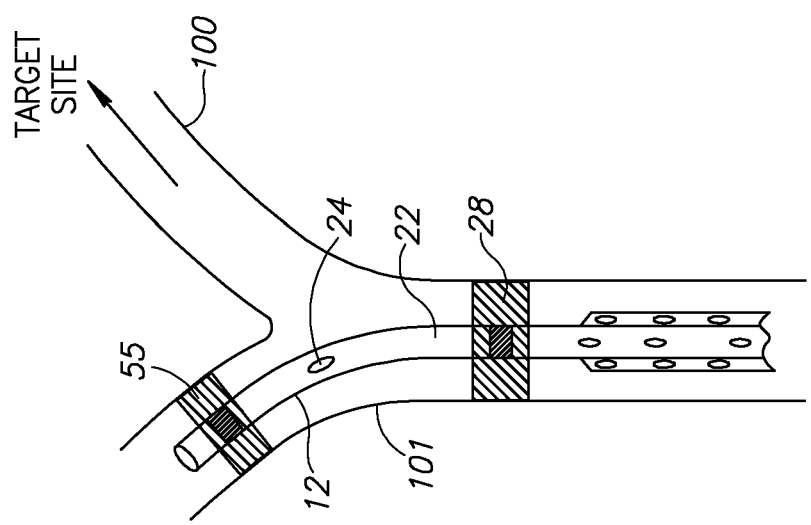
Figure 13A:
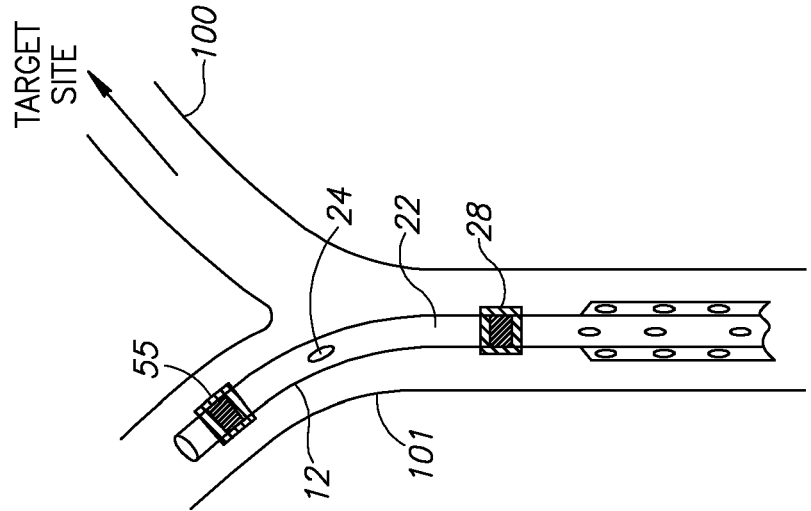

Reference is now made to FIGS. 13A-C, which are illustrations of a method for treating a specific target site in accordance with yet another embodiment of the present invention. As shown in FIG. 13A, catheter 12 is inserted into a blood vessel, and advanced to a secondary vessel 101 which is near vessel 100. For example, vessel 100 and secondary vessel 101 can be branches of a main vessel. This method may be desirable, for example, if vessel 100 is diseased and might be adversely affected by introduction of a foreign element such as a catheter therein. In a preferred embodiment, wherein the goal is to selectively cool the brain without induction of systemic hypothermia, the target site is the brain, and secondary vessel 101 is the carotid artery (right or left, common, internal or external). A position of catheter 12 within vessel 101 is monitored by radiopaque marker 48. When catheter 12 is in the desired location, occlusion element 28 and distal occlusion element 55 are expanded, as shown in FIG. 13B. Expansion of occlusion elements 28 and 55 serves to isolate blood vessel 100 which leads to the target site, and anchors catheter 12 in place without placing catheter 12 directly in blood vessel 100. Reference is now made to FIG. 13C, which illustrates the flow of blood. Once occlusion elements 28 and 55 are deployed, normothermic blood, represented by arrows 44, enters supply elongated element 20 via inlet ports 26. It should be readily apparent that although the method depicted in FIGS. 12A-12C shows supply elongated element 20 having multiple inlet ports and positioned in a vessel in such a way so as to collect antegrade blood, these depictions should not be regarded as limiting. In alternative embodiments, as described above with reference to FIGS. 1B, 8H and 9H, supply elongated element 20 may have one inlet port, and it may be positioned within the aortic arch. Normothermic blood flows through supply lumen 120, out through inlet connector 32 of hub 30 and through supply blood inlet 34 into control unit 14. Control unit 14 then heats or cools the blood to form thermally altered blood, which is pumped out through delivery blood outlet 38, through outlet connector 36, and into delivery elongated element 22. Thermally altered blood, represented by broken arrow 46, flows out through exit port 24 and into the portion of the blood vessel which leads to the target site. In one embodiment, pharmaceuticals are simultaneously administered to the target site via drug infusion port. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application.

It should be readily apparent that a single catheter serves to both collect and deliver the normothermic and thermally altered blood. In an additional embodiment, all or some blood contact surfaces can be coated with an anti thrombotic substance such as heparin.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for selectively cooling or heating a part of a body, the method comprising:
   providing a device for insertion into a vessel, the device comprising a first lumen and an exit port, a second lumen and a second port, said second lumen positioned coaxial to said first lumen and extending along a majority of a length of said first lumen, and an occlusion element positioned between said exit port and said second port;
   inserting said device into a vessel;
   expanding said occlusion element so as to separate between a first area in fluid communication with said exit port and a second area in fluid communication with said second port;
   withdrawing normothermic blood from said second area via said second port and through said second lumen;
   delivering said normothermic blood to a control unit;
   thermally treating said normothermic blood in said control unit to obtain thermally treated blood; and
   delivering said thermally treated blood to said first area via said first lumen and said exit port.

2. The method of claim 1, wherein said thermally treating comprises cooling.

3. The method of claim 1, wherein said thermally treating comprises heating.

4. The method of claim 1, wherein said delivering said thermally treated blood comprises pumping said thermally treated blood.

5. The method of claim 1, further comprising delivering a second thermally treated blood to a location in the body, said second thermally treated blood having a different temperature than said thermally treated blood.

6. The method of claim 1, further comprising monitoring a physiological parameter; and adjusting said thermally treating based on said monitored parameter.

7. The method of claim 1, wherein said providing a device comprises:
   positioning a guidewire in a proximal artery, said proximal artery being proximal to a target artery;
   introducing a search catheter over said guidewire;
   partially withdrawing said guidewire;
   locating the target artery with said search catheter;
   advancing said guidewire through said search catheter and into the target artery;
   removing the search catheter; and
   advancing a distal end of said device over the guidewire into the target artery.

8. The method of claim 7, wherein said target artery is a carotid artery, and wherein said advancing comprises advancing into the carotid artery.

9. The method of claim 7, wherein said target artery is a renal artery, and wherein said advancing comprises advancing into the renal artery.

10. The method of claim 7, wherein said target artery is a coronary artery, and wherein said advancing comprises advancing into the coronary artery.

11. The method of claim 7, further comprising introducing a supply elongated element over said guidewire, and wherein said introducing said search catheter is done through a lumen of said supply elongated element.

12. The method of claim 7, wherein said positioning comprises positioning in an aortic arch.

13. The method of claim 7, wherein said introducing a search catheter includes introducing a search catheter through said first lumen of said device.

14. The method of claim 7, wherein said introducing a search catheter includes introducing a delivery elongated element of said device, wherein said delivery elongated element has a bent distal end for locating a vessel.

15. The method of claim 7, wherein said advancing said guidewire through said search catheter and into the carotid artery includes advancing said guidewire into an external carotid artery, and advancing a distal end of said device into the carotid artery includes advancing said distal end into the external carotid artery.

16. The method of claim 7, wherein said advancing said guidewire through said search catheter and into the carotid artery includes advancing said guidewire into an internal carotid artery, and advancing a distal end of said device into the carotid artery includes advancing said distal end into the internal carotid artery.

17. A method for insulating thermally treated blood for delivery to a location in a body, the method comprising:
   providing a delivery catheter having a delivery lumen and a supply lumen which is coaxial to said delivery lumen, said supply lumen extending along a majority of said delivery lumen;
   inserting said delivery catheter into the arterial system;
   withdrawing normothermic blood from the arterial system via said supply lumen;
   thermally treating said withdrawn blood;
   simultaneously to said withdrawing, providing thermally treated blood via said delivery lumen to the arterial system, said simultaneous providing being in a location which is distal to a location of said withdrawing,
   wherein said withdrawing is done coaxial to said providing thermally treated blood, thus providing a layer of insulation to said thermally treated blood.

18. The method of claim 17, wherein said thermally treating comprises cooling.

19. The method of claim 17, wherein said thermally treating comprises heating.

20. The method of claim 17, wherein said providing said thermally treated blood comprises pumping said thermally treated blood.

21. The method of claim 17, further comprising delivering a second thermally treated blood to a location in the body, said second thermally treated blood having a different temperature than said thermally treated blood.

22. The method of claim 17, further comprising monitoring a physiological parameter; and adjusting said thermally treating based on said monitored parameter.

* * * * *